United States Patent
O'Lenick, Jr. et al.

(10) Patent No.: US 6,979,744 B1
(45) Date of Patent: Dec. 27, 2005

(54) DIMER AMIDOPROPYL DIMETHYL BETAINES

(75) Inventors: Anthony J. O'Lenick, Jr., Dacula, GA (US); Thomas G. O'Lenick, Knoxville, TN (US); Kevin A. O'Lenick, Canton, GA (US)

(73) Assignee: SurfaTech Corporation, Dacula, GA (US)

(*) Notice: Subject to any disclaimer, the term of this patent is extended or adjusted under 35 U.S.C. 154(b) by 80 days.

(21) Appl. No.: 10/797,145

(22) Filed: Mar. 11, 2004

(51) Int. Cl.$^7$ .................. C07C 233/00; C07C 239/00

(52) U.S. Cl. ..................... 554/63; 554/35; 564/152

(58) Field of Search ............... 554/35, 63; 564/152

(56) References Cited

U.S. PATENT DOCUMENTS 6,331,293 B1    12/2001   Smith et al.

FOREIGN PATENT DOCUMENTS

JP          04-202336     *   7/1992

\* cited by examiner

*Primary Examiner*—Cecilia J. Tsang
*Assistant Examiner*—Taylor Victor Oh

(57) ABSTRACT

The present invention relates to a class of compounds having specific betaines based upon a dimer acid amido amine. Dimer acid is a C-36 diacid having a cyclic structure and two amine groups that allow for the synthesis of a high molecular weight material quaternary compound which is extremely substantitive to human skin and are well tolerated by human tissue making them suitable for use preparation of personal care products.

2 Claims, No Drawings

DIMER AMIDOPROPYL DIMETHYL BETAINES

FIELD OF THE INVENTION

The present invention relates to a novel class of compounds having specific betaine compounds based upon a dimer acid amido amine. Dimer acid is a C-36 diacid having a cyclic structure and two amine groups that allow for the synthesis of a high molecular weight cationic compound which is extremely substantitive to human skin and are well tolerated by human tissue making them suitable for use preparation of conditioning amphoterics for personal care applications.

BACKGROUND OF THE INVENTION

It is very desirable to provide a material from aqueous solution that will condition the hair and still be compatible with anionic surfactants. This allows for the preparation of clear two in one shampoo systems, clear 2 in one shower gels, and clear two in one bath products. By two in one products in meant, a product that contains both anionic surfactant, most commonly sulfates and ether sulfates and a cationic conditioning agent. The anionic surfactant is the detergent, which cleans the hair or skin, and the cationic product is for conditioning providing softness, slip and feels to the skin. The problem with such product has always been the incompatibility of the anionic and cationic surfactants with each other. When many of these products are present in the same solution an insoluble salt forms making a cosmetically unacceptable white gunk that does not stay in solution.

As will become clear, by making a very large molecule the present invention results in a betaine that exhibits detergency, foam and conditioning in the same molecule. When these betaine compounds are placed in water along with the anionic surfactant, a clear stable solution is obtained.

The molecules of the present invention are truly multifunctional. They provide detergency. Foam and conditioning in surfactant systems. This makes them quite desirable in personal care products. Betaines are specific members of a class of compounds called amphoteric surfactants. They can exist only as amphoterics and cationic products over a wide range of pH. This is because the tetra substitution pattern around nitrogen makes the positive charge on nitrogen a permanent feature of the molecule regardless of pH.

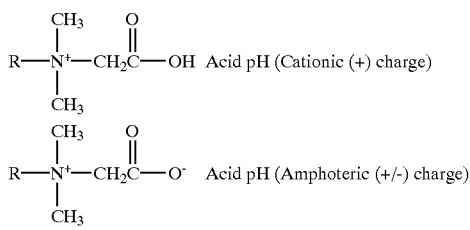

The compounds of the present invention can be formulated into body washes and other skin products and hair care products to provide a "delivery system" for conditioning the hair or skin. The high molecular weight of the product and the fact that they are amphoterics, results in through and efficient deposition on the hair or skin. This provides uniformity of conditioning agent over the entire hair of skin surface. This is particularly important for applications on hair for people with long hair. In general the long hair has at it's tip areas that are more damaged, dry and in need of conditioning. The hair closest to the scalp is newer, less damaged, and less in need of conditioning. This dichotomy of hair condition is more effectively treated by the compounds of the present invention than by other betaines.

U.S. Pat. No. 6,331,293 issued Dec. 18, 2001 to Smith et al describes phosphobetaines that are derived from dimer acid. Unlike the compounds of the present invention, these materials are amphoteric surfactants and are barriers when applied to the skin. It is stated that the compounds are "extremely substantitive to human skin and are well tolerated by human tissue making them suitable for use preparation of barrier products for personal care applications". Unlike these materials, the compounds of the present invention contain no phosphate group and are conditioning agents, detergents and foaming agents.

SUMMARY OF THE INVENTION

Objective of the Invention

It is the objective of the invention to provide a novel dimer acid based amido betaines and a process of its use which comprises contacting the skin with an effective conditioning concentration of the novel compounds.

In accordance with the present invention, we have now been discovered novel betaine compound, which conforms to one of the following structures:

The first structure is:

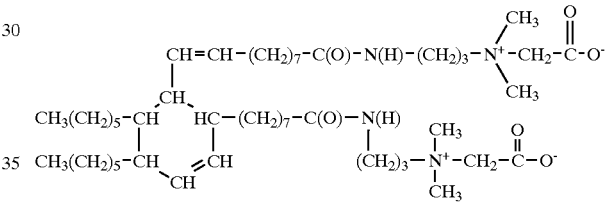

The second closely related structure is:

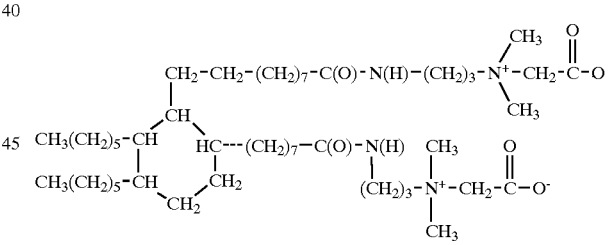

The difference between the two is the second has no double bond in the cyclic structure, while the first has a double bond. The double bond is removed by hydrogenation of the acid prior to making the quaternary compound. This variation has lighter color and better oxidative stability, making it prized for cosmetic applications where a water white product is desired. Consumers consider water white products as cleaner and more appealing over yellow products.

The present invention is also directed to a process for very efficiently cleaning and simultaneously conditioning the skin and hair from aqueous solution. The product is very efficient in providing conditioning and can be used at concentrations as low as 0.5% by weight in a shampoo formulation. This is very important in products where low irritation is important like baby shampoo and bubble bath products.

DETAILED DESCRIPTION OF THE INVENTION

The present invention is directed to novel betaine compounds, which conform to one of the following structure:

The first structure is:

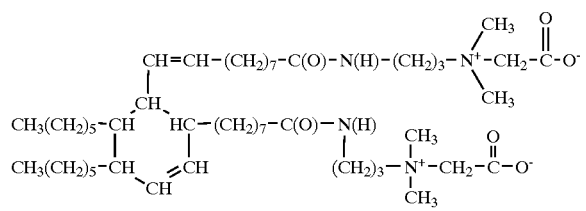

The second closely related structure is:

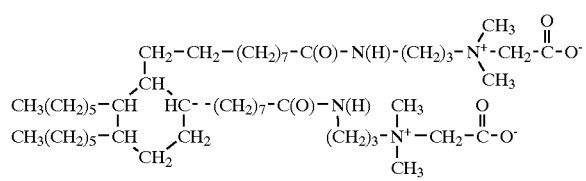

The compounds of the present invention are prepared by reacting first reacting dimer acid with dimethylaminopropyl amine (DMAPA) to give a tertiary amine intermediate.

The first structure is:

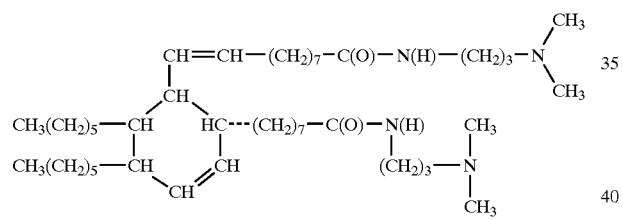

The second closely related structure is:

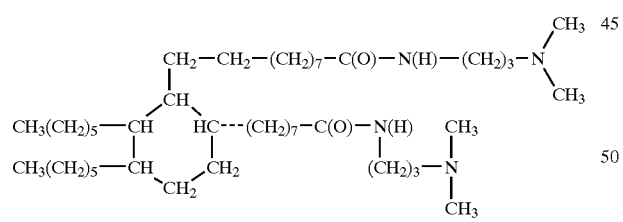

In a subsequent step, the dimer DMAPA product is reacted with sodium monochloro-acetate to give the compounds of the present invention.

Sodium monochloroacetate is also called chloroacetic acid sodium salt and conforms to the following structure Cl-CH$_2$-C(O)O$^-$Na$^{30}$ The compounds of the present invention are made reaction of the sodium monochloroacetate under aqueous conditions. The product of the invention is thereby attained.

The compatibility of this novel compounds of the invention with human tissue, i.e., dermal and eye tissue has been tested. In these tests, 48-hour human patch dermal evaluations (5% in water), in vitro ocular evaluations (3% in water) and repeated insult patch tests (3% in water) determined that the compounds are substantially non-irritating to humans, they are safe and suitable for use in eye area products and are not a skin sensitizer to humans.

EXAMPLES

Dimer Acid and Hydrogenated Dimer Acid

Dimer acid and hydrogenated dimer acid are items of commerce commercially available from several suppliers, one of which is Cognis Corporation, formerly the Emery Division of Henkel.

Dimer acid conforms to the following structure;

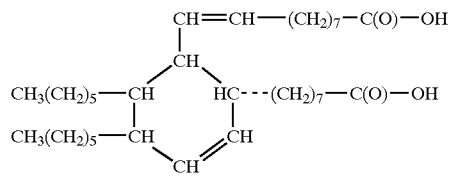

Hydrogenated dimer acid conforms to the following structure;

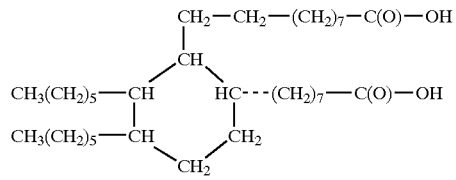

DMAPA

Dimethylaminopropyl Amine is an item of commerce available from a variety of sources including Dow Chemical.

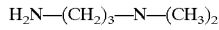

Sodium Monochloroacetate

Sodium monochloroacetate is an item of commerce. It conforms to the following structure:

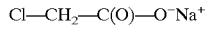

EXAMPLE 1

Preparation of Dimer Amido Amine

To 561.0 grams if dimer acid is added 153.0 grams of dimethylaminopropyl amine. The mixture is heated to 180–200° C. and held for 3–8 hours. Once the temperature begins to reach 180° C., water begins to distill off. An excess of dimethylaminopropyl amine is added to speed up the reaction. When the acid value reaches 1.0 mg KOH/gram, the excess dimethylaminopropyl amine is stripped off by applying vacuum. The resulting product is the dimer amido amine useful as an intermediate in the preparation of the compounds of the present invention. The alkali value of the product so produced is 180.0 mg KOH/gm. The product is a yellow water insoluble liquid at ambient temperatures.

EXAMPLE 2

Preparation of Dimer Amido Amine

To 563.0 grams if hydrogenated dimer acid is added 153.0 grams of dimethylaminopropyl amine. The mixture is heated to 180–200° C. and held for 3–8 hours. Once the temperature begins to reach 180° C., water begins to distill off. An excess of dimethylaminopropyl amine is added to speed up the reaction. When the acid value reaches 1.0 mg KOH/gram, the excess dimethylaminopropyl amine is stripped off by applying vacuum. The resulting product is the dimer amido amine useful as an intermediate in the preparation of the compounds of the present invention. The alkali value of the product so produced is 180.0 mg KOH/gm.

EXAMPLE 3

Preparation of the Betaine of the Present Invention

Into a suitable reaction flask is charged 937.0 grams of de-ionized water. Next, add 238.0 grams of sodium chloro acetate. Heat is applied to 90° C. Next, 625.0 grams of dimer amidoamine (example 1) are charged into the reaction vessel under good agitation. The temperature is maintained at between 90° C. and 95° C., until the percentage of free tertiary amine is 0.5% maximum. During the reaction time, the pH is kept at between 7 and 8 with NaOH as required. The reaction mass will clear when the product is at 90 C for about 1 hour. The reaction time is approximately 6 to 9 hours. The % NaCl is monitored and the reaction is deemed complete when the % of theoretical NaCl reaches 98%.

The compound of the present invention is used without additional purification. It is a clear viscous liquid and is sold as an aqueous solution of between 30 and 40% solids by weight.

EXAMPLE 4

Preparation of the Cationic of the Present Invention

Into a suitable reaction flask is charged 937.0 grams of de-ionized water. Next, add 238.0 grams of sodium chloro acetate. Heat is applied to 90° C. Next, 625.0 grams of dimer amidoamine (example 2) are charged into the reaction vessel under good agitation. The temperature is maintained at between 90° C. and 95° C., until the percentage of free tertiary amine is 0.5% maximum. During the reaction time, the pH is kept at between 7 and 8 with NaOH as required. The reaction mass will clear when the product is at 90 C for about 1 hour. The reaction time is approximately 6 to 9 hours. The % NaCl is monitored and the reaction is deemed complete when the % of theoretical NaCl reaches 98%.

The compound of the present invention is used without additional purification. It is a clear viscous liquid and is sold as an aqueous solution of between 30 and 40% solids by weight.

Applications Examples

The compounds of the present invention show good detergency, conditioning and foam in shampoos.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. A betaine compound conforming to the following structure:

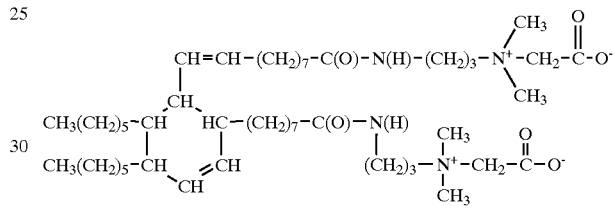

2. A betaine compound conforming to the following structure:

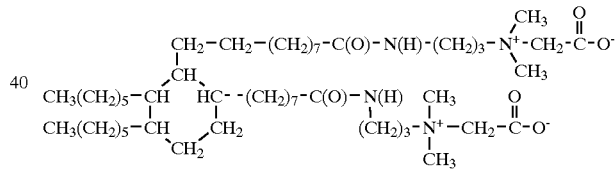

* * * * *